(12) United States Patent
Yang et al.

(10) Patent No.: US 11,630,051 B2
(45) Date of Patent: Apr. 18, 2023

(54) METHOD FOR INVERTING AEROSOL COMPONENTS USING LIDAR RATIO AND DEPOLARIZATION RATIO

(71) Applicant: Institute of Atmospheric Physics, Chinese Academy of Sciences, Beijing (CN)

(72) Inventors: Ting Yang, Beijing (CN); Zifa Wang, Beijing (CN); Futing Wang, Beijing (CN); Xi Chen, Beijing (CN); Haibo Wang, Beijing (CN); Hongyi Li, Beijing (CN)

(73) Assignee: INSTITUTE OF ATMOSPHERIC PHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/658,355

(22) Filed: Apr. 7, 2022

(65) Prior Publication Data

US 2022/0334045 A1    Oct. 20, 2022

(30) Foreign Application Priority Data

Apr. 7, 2021  (CN) .......................... 202110375211.3

(51) Int. Cl.
   *G01N 15/14*   (2006.01)
   *G01N 33/00*   (2006.01)
   *G01S 17/88*   (2006.01)

(52) U.S. Cl.
   CPC ..... *G01N 15/1429* (2013.01); *G01N 15/1434* (2013.01); *G01N 33/0062* (2013.01); *G01S 17/88* (2013.01)

(58) Field of Classification Search
   CPC .......... G01N 15/1429; G01N 15/1434; G01N 33/0062; G01S 17/88
   (Continued)

(56) References Cited

U.S. PATENT DOCUMENTS 7,580,127 B1 *  8/2009  Mayor ................... G01N 21/21
                                                          356/337
2021/0311087 A1 * 10/2021 Miyashita .............. G01N 21/47

FOREIGN PATENT DOCUMENTS

CN          113189563 A  *  7/2021  ............. G01N 15/00

OTHER PUBLICATIONS

Florian Gaudfrin et al; "A new lidar inversion method using a surface reference target. Application to the backcattering coefficient and lidar ratio retrievals of a fog-oil plume at short-range."; Atmospheric Measurement Techniques; 2019; https://doi.org/10.5194/amt-2019-315 (Year: 2019).*

(Continued)

*Primary Examiner* — Roy M Punnoose
(74) *Attorney, Agent, or Firm* — Muncy, Geissler, Olds & Lowe, P.C.

(57) ABSTRACT

A method for inverting aerosol components using a LiDAR ratio and a depolarization ratio, includes: S1. identifying sand dust, a spherical aerosol and a mixture of the sand dust and the spherical aerosol based on a depolarization ratio; S2. calculating a proportion of the sand dust in the mixture of the sand dust and the spherical aerosol; and S3. identifying soot and a water-soluble aerosol in the spherical aerosol based on a LiDAR ratio. In the present disclosure, only a wavelength with a polarization channel is needed, to identify the aerosol components, achieving high accuracy with low detection costs.

7 Claims, 6 Drawing Sheets

(58) Field of Classification Search
USPC .......................................................... 702/24
See application file for complete search history.

(56) References Cited

OTHER PUBLICATIONS

Burton et al., "Aerosol classification using airborne High Spectral Resolution Lidar measurements—methodology and examples," Atmosphere Measurement Techniques (2012); 5: 73-98.
Mamouri et al., "Fine and coarse dust separation with polarization lidar," Atmosphere Measurement Techniques (2014); 7: 3717-3735.
Müller et al., "Aerosol-type-dependent lidar ratios observed with Raman lidar," Journal of Geophysical Research (2007); 112(D16202): 1-11.
Murayama et al., "Characterization of Asian dust and Siberian smoke with multi-wavelength Raman lidar over Tokyo, Japan in spring 2003," Geophysical Research Letters (2004); 31(L23103): 1-5.
Sakai et al., "Backscattering linear depolarization ratio measurements of mineral sea-salt and ammonium sulfate particles simulated in a laboratory chamber," Applied Optics (2010); 49(23): 4441-4449.
Tesche et al., "Particle backscatter, extinction, and lidar ratio profiling with Raman lidar in south and north China," Applied Optics (2007); 46(25): 6302-6308.
Xie et al., "Characteristics of aerosol optical properties in pollution and Asian dust episodes over Beijing, China," Applied Optics (2008); 47(27): 4945-4951.

* cited by examiner

```
┌─────────────────────────────────────────────┐
│  establishing a lookup table 1 for the      │
│ extinction coefficient with respect to an   │ S41
│ extinction coefficient of a water-soluble   │
│ aerosol and an extinction coefficient of    │
│ soot, and establishing an additional        │
│ lookup table 2 with respect to a case that  │
│ the extinction coefficient is greater than 1│
└─────────────────────────────────────────────┘
                      │
                      ▼
┌─────────────────────────────────────────────┐
│ combining the lookup table for the          │ S42
│ extinction coefficient with the LiDAR ratio │
│ to establish a lookup table for a           │
│ backscattering coefficient :                │
└─────────────────────────────────────────────┘
                      │ S43
                      ▼
              ◇ 0 < σ_sphere ≤ 1 ◇ ──Y──▶ traversing the lookup table 1
                      │ N
                      ▼
              ◇ 1 < σ_sphere ≤ 3 ◇ ──Y──▶ traversing the lookup table 2
                      │ N
                      ▼
┌─────────────────────────────────────────────┐
│ selecting as an optimal solution a solution │ S44
│ ensuring a minimum deviation between an     │
│ observed value and a theoretical value,     │
│ that is, a solution meeting the following   │
│ condition                                   │
└─────────────────────────────────────────────┘
```

METHOD FOR INVERTING AEROSOL COMPONENTS USING LIDAR RATIO AND DEPOLARIZATION RATIO

CROSS REFERENCE TO RELATED APPLICATION

This patent application claims the benefit and priority of Chinese Patent Application No. 202110375211.3, filed on Apr. 7, 2021, the disclosure of which is incorporated by reference herein in its entirety as part of the present application.

TECHNICAL FIELD

The present disclosure relates to the technical field of atmospheric environment monitoring, and in particular, to a method for inverting aerosol components using a LiDAR ratio and a depolarization ratio.

BACKGROUND ART

A LiDAR ratio (S) is a ratio of an extinction coefficient to a backscattering coefficient, and is calculated using an equation: $S_i = \sigma_i/\beta_i$ (1), where i represents different aerosol components; $\sigma_i$ represents extinction coefficients of the different components; $\beta_i$ represents backscattering coefficients of the different components. The LiDAR ratio is an important parameter for identifying aerosol components. Different types of aerosols have significantly different LiDAR ratios. As disclosed in previous study, sand-dust particles from Asia or the Sahara have a LiDAR ratio of approximately 50 sr (Burton et al., 2012; Murayama et al., 2004). LiDAR ratios of pure sand-dust particles are different mainly due to their different source regions. Based on observed results, usually, aerosol particles with stronger absorbency, such as black carbon (BC), have larger LiDAR ratios that mainly range from 70 sr to 80 sr (Burton et al., 2012; Mueller et al., 2007). In the case that discharge of waste causes pollution in the region, haze particles usually have LiDAR ratios that mainly ranges from 45 sr to 60 sr (Mueller et al., 2007; Tesche et al., 2007; Xie et al., 2008). The value is close to the LiDAR ratio of the sand-dust particles, and therefore, to accurately separate the sand dust from water-soluble aerosol particles, other LiDAR parameters are still needed.

The depolarization ratio ($\delta$) is a ratio of a vertical polarization component to a horizontal polarization component of a LiDAR signal, and is calculated using an equation: $\delta = P_r/P_l$ (2), where $P_r$ and $P_l$ are separately the vertical polarization component and the horizontal polarization component of the signal. A NIES Miescattering LiDAR system has a polarizer with a 45° polarization direction for a 532 nm signal, which can separate a horizontal signal from a vertical signal. The depolarization ratio is a parameter that can directly reflect a shape of the aerosol particles. The greater the depolarization ratio, the more irregular the particle shape. According to laboratory results by Sakai et al. (2010), sand-dust particles mainly in a coarse mode have a depolarization ratio of 0.39±0.04 for the 532 nm signal. This is consistent with a characteristic of sand-dust particles detected outside the laboratory, and the sand-dust particles from Asia or the Sahara has a depolarization ratio of approximately 0.3 to 0.35 (Burton et al., 2012; GroB et al., 2011; Xie et al., 2008). However, aerosols in urban regions and absorptive aerosols produced after combustion of biological substances have a smaller size and a smaller depolarization ratio, which is usually less than 0.1 to 0.2 (Burton et al., 2012; Mamouri and Ansmann, 2014; Sakai et al., 2010; Xie et al., 2008). Therefore, it is believed that a material having a depolarization ratio of 0.2 to 0.35 is a mixture of the sand dust and other substances.

The Miescattering theory is proposed with respect to scattering of homogeneous spherical particles, and is derived from Maxwell's equations as an exact solution to scattering of plane waves by the homogeneous spherical particles in an electromagnetic field. Usually, scattering caused by microparticles whose particle diameter is equivalent to a wavelength of incident light 101 is referred to as Miescattering. When particle diameter distribution and complex refractive indexes of different types of aerosols are provided, an extinction coefficient and a backscattering coefficient of different aerosol components can be calculated according to the Miescattering theory, so as to obtain a LiDAR ratio of different types of aerosols.

Derived from the Miescattering theory, both expressions of a backscattering efficiency factor $Q_b$ and an extinction efficiency factor $Q_e$ of a single spherical particle are as follows:

$$Q_e = \frac{2}{x^2}\sum_{n=1}^{\infty}(2n+1)\mathrm{Re}(a_n + b_n) \tag{3}$$

$$Q_b = \frac{1}{x^2}\left|\sum_{n=1}^{\infty}(2n+1)(-1)^n(a_n - b_n)^2\right| \tag{4}$$

where $$x = \frac{2\pi r}{\lambda},$$

r represents a particle radius, $\lambda$ represents a laser wavelength; and $a_n$ and $b_n$ represent complex coefficients and are related to the particle radius and a negative refractive index. Therefore, to calculate the extinction efficiency factor and the backscattering efficiency factor of the single particle, only the particle radius and the complex refractive index are required.

The extinction coefficient and the backscattering coefficient of aerosols of a specific mass concentration can be further calculated based on calculated values of $Q_e$ and $Q_b$. In this way, when the particle size distribution remains unchanged, the extinction coefficient and the backscattering coefficient (measured in $m^{-1}$) of atmospheric aerosols can be determined. Expressions of the extinction coefficient $\beta_e$ and the backscattering coefficient $\beta_b$ are as follows:

$$\beta_e = \int_{+\infty}^{-\infty}\frac{3}{4r}\frac{dV(r)}{d\ln r}Q_e\left(\frac{2\pi r}{\lambda}, m\right)d\ln r. \tag{5}$$

$$\beta_b = \int_{+\infty}^{-\infty}\frac{3}{4r}\frac{dV(r)}{d\ln r}Q_b\left(\frac{2\pi r}{\lambda}, m\right)d\ln r \tag{6}$$

where $$\frac{dV(r)}{d\ln r}$$

represents aerosol volume distribution:

$$\frac{dV(r)}{d\ln r} = \frac{V_0}{\sqrt{2\pi}\ln\sigma}\exp\left(-\frac{1}{2}\left(\frac{\ln r - \ln r_v}{\ln\sigma}\right)^2\right), \quad (7)$$

$V_0$ represents a total volume concentration of aerosol particles; $r_v$ represents a volume geometric mean radius; and $\sigma$ represents a volume standard deviation.

Table 1 shows a LiDAR ratio obtained based on particle size distribution and complex refractive indexes of three aerosols of soot (mainly absorbing aerosol BC), the water-soluble aerosol (mainly sulfate and nitrate), and the sand dust provided in a previous study (Dey et al., 2006; Ganguly et al., 2009; Hess et al., 1998; van Beelen et al., 2014) with reference to the Miescattering theory. It can be found that the LiDAR ratio of the soot is approximately twice that of the water-soluble aerosol, and therefore, the soot and the water-soluble aerosol can be identified using the LiDAR ratios. However, due to sphere assumption in the Miescattering theory, the calculated LiDAR ratio of the sand dust is not consistent with an actual result in field observation. During actual observation, the sand dust is usually an irregular non-spherical particle. It should be noted that the actually observed LiDAR ratio (Burton et al., 2012; Murayama et al., 2004) is close to that of the water-soluble aerosol, but the sand dust and the water-soluble aerosol have significantly different depolarization ratios. Therefore, in an inversion algorithm, the sand dust can be first separated from the spherical aerosol using a non-spherical characteristic of the sand dust, and then the soot can be distinguished from the water-soluble aerosol using significantly different LiDAR ratios.

TABLE 1

Microphysical paramaeters used in an inversion algorithm

| type | $r_m$ | $s_d$ | $m_r$ | $m_i$ | S | $\delta$ | reference |
|---|---|---|---|---|---|---|---|
| Soot | 0.095 | 1.8 | 1.85 | 0.71 | 85 | 0.05 | Ganguly et al. (2009) van Beelen et al. (2014) Burton et al. (2012) |
| Water-soluble | 0.17 | 2 | 1.53 | $1 \times 10^{-7}$ | 47 | 0.05 | Ganguly et al. (2209) van Beelen et al. (2014) and Dey et al. (2006) and Sugimoto et al. (2003) |
| Dust | 3 | 2.2 | 1.53 | $6.3 \times 10^{-3}$ | 21 | 0.31 | van Beelen et al. (2014) and Hess et al. (1998) and Mamouri et. al. (2014) |

Herein, $r_m$ represents a volume average radius (measured in um); $s_d$ represents the volume standard deviation (measured in um); $m_r$ represents a real part of the complex refractive index; $m_i$ represents an imaginary part of the complex refractive index; S represents the LiDAR ratio; and $\delta$ represents the depolarization ratio.

SUMMARY

To solve the technical problems, the present disclosure provides a method for inverting aerosol components using a LiDAR ratio and a depolarization ratio, providing a feasible technical solution for a vertical study on aerosol components during atmospheric environment monitoring.

To solve the above technical problems, the present disclosure provides the following technical solutions:

A method for inverting aerosol components using a LiDAR ratio and a depolarization ratio is provided, including:

S1. identifying sand dust, a spherical aerosol and a mixture of the sand dust and the spherical aerosol based on a depolarization ratio;

S2. calculating a proportion of the sand dust in the mixture of the sand dust and the spherical aerosol; and S3. identifying soot and a water-soluble aerosol in the spherical aerosol based on a LiDAR ratio.

Further, step S1 includes: calculating an aerosol depolarization ratio ADR, where when the ADR is greater than a, the aerosol components are considered to be the sand dust; when b≤ADR≤a, the aerosol components are considered to be the mixture of the sand dust and the spherical aerosol; or when the ADR is less than b, the aerosol components are considered to be the spherical aerosol.

Further, the calculating the ADR includes: directing a LiDAR signal through a polarizer with a 45° polarization direction at a 532 nm signal using a NIES Miescattering LiDAR system, to separate a horizontal signal from a vertical signal.

Further, a=0.31 and b=0.05.

Further, step S2 includes steps of:

S21. setting depolarization ratios of the sand dust and the spherical aerosol as $\delta_1$ and $\delta_2$ respectively, and defining the depolarization ratios of the two components as $\delta_i = P_{i\perp}/P_{i\parallel}$, where $P_{i\perp}$ and $P_{i\parallel}$ are vertical and horizontal components of an aerosol backscattered signal respectively;

S22. defining $\delta_i' = P_{i\perp}/(P_{i\perp}+P_{i\parallel})$, then $\delta_i' = \delta_i/(i+1)$; and S23. assuming that x represents an optical proportion of the sand dust in an aerosol mixture, where a polarization component of the backscattered signal is expressed as:

$$P_\perp = [x\delta_1' + (1-x)\delta_2']P$$

$$P_\parallel = [x(1-\delta_1') + (1-x)(1-\delta_2')]P$$

where $P = P_\perp + P_\parallel$, and therefore, the aerosol depolarization ratio S is expressed as:

$$\delta = \frac{P_\perp}{P_\parallel} = \frac{x\delta_1' + (1-x)\delta_2'}{x(1-\delta_1') + (1-x)(1-\delta_2')}$$

and therefore, the optical proportion of the sand dust x can be calculated using an equation:

$$x = \frac{(\delta - \delta_2)(1+\delta_1)}{(1+\delta)(\delta_1 - \delta_2)}$$

Further, the aerosol depolarization ratio S is obtained through the following steps:

assuming $$R = \frac{\beta_1 + \beta_2}{\beta_2},$$

where $\beta_1$ represents a backscattering coefficient of an aerosol particle, and $\beta_2$ represents a backscattering coefficient of an atmospheric molecule; and $$\delta = \frac{(1+\delta_m)\delta_v R - (1+\delta_v)\delta_m}{(1+\delta_m)R - (1+\delta_v)}$$

substituting R into the equation:

$$\delta = \frac{(1+\delta_m)\delta_v R - (1+\delta_v)\delta_m}{(1+\delta_m)R - (1+\delta_v)}$$

where $\delta_v$ represents a signal depolarization ratio, and $\delta_m$ represents a molecule depolarization ratio.

Further, $\beta_1$ is obtained through the following steps:

measuring the Miescattering caused by the aerosol and the Rayleigh scattering caused by the atmospheric molecule separately, where a LiDAR equation is expressed as $$P(z) = CP_0 z^{-2}[\beta_1(z) + \beta_2(z)]\exp[-2\int_0^z \sigma_1(z)dz]\exp[-2\int_0^z \sigma_2(z)dz]$$

where C represents a radar correction constant; $P_0$ represents radar transmission power; and $\beta$ represents the backscattering coefficient, $\sigma$ represents an extinction coefficient, and subscripts of 1 and 2 represent the aerosol particle and the atmospheric molecule respectively;

assuming that a relationship between the extinction coefficient $\sigma$ and the backscattering coefficient $\beta$ is as follows:

$$S = \sigma/\beta$$

and solving the foregoing LiDAR equation gives:

$$\beta_1 = -\beta_2 + \frac{X(z)\exp\left[-2(S_1 - S_2)\int_{z_c}^z \beta_2(z)dz\right]}{\frac{X(z_c)}{\beta_1(z_c) + \beta_2(z_c)} - 2S_1\int_{z_c}^z P(z)z^2\exp\left[-2(S_1 - S_2)\int_{z_c}^z \beta_2(z')dz'\right]dz}$$

where $X(z) = P(z)z^2$; and $\beta_1(z_c)$ and $\beta_2(z_c)$ are boundary values at a far end $z_c$.

Further, step S3 includes:

S31. establishing a lookup table 1 for the extinction coefficient $\alpha$ with respect to an extinction coefficient $\sigma_{ws}$ of a water-soluble aerosol and an extinction coefficient $\sigma_{st}$ of soot, and establishing an additional lookup table 2 with respect to a case that the extinction coefficient is greater than 1;

S32. combining the lookup table for the extinction coefficient with the LiDAR ratio to establish a lookup table for a backscattering coefficient $\beta$:

$$\beta = \frac{\sigma_{ws}}{S_1} + \frac{\sigma_{st}}{S_2}$$

S33. if $0 < \sigma_{sphere} \leq 1$, traversing the lookup table 1, or if $1 < \sigma_{sphere} \leq 3$, traversing the lookup table 2, where $\sigma_{sphere}$ is an extinction coefficient for the spherical aerosol, $\sigma_{sphere}$ is the backscattering coefficient; and retrieving an array of extinction coefficients from the lookup table whose errors relative to observed values meet a standard:

$$\left|\frac{\sigma_{sphere} - \sigma}{\sigma_{sphere}}\right| < 0.01$$

$$\left|\frac{\beta_{sphere} - \beta}{\beta_{sphere}}\right| < 0.01$$

and S34. if the lookup table does not match the observed values, selecting as an optimal solution a solution ensuring a minimum deviation between an observed value and a theoretical value, that is, a solution meeting the following condition:

$$\min\left(\sqrt{\left|\frac{\sigma_{sphere} - \sigma}{\sigma_{sphere}}\right|^2 + \left|\frac{\beta_{sphere} - \beta}{\beta_{sphere}}\right|^2}\right)$$

Further, in step S33, the extinction coefficient $\sigma_{sphere}$ of the spherical aerosol is equal to $(1-x)\sigma$.

Compared with the prior art, the present disclosure has the following beneficial effects.

During the existing atmospheric environment monitoring, it is only possible to determine whether there are the aerosol components, and amounts of contained aerosol components cannot be determined. The present disclosure fills the gap in this field. In the prior art, to identify the aerosol components, complex and expensive devices and complex operations are required, however, detection results are apt to be inaccurate. On the contrary, in the present disclosure, only a wavelength with a polarization channel is needed, to identify the aerosol components, achieving high accuracy with low detection costs.

DETAILED DESCRIPTION OF THE EMBODIMENTS

The specific embodiments of the present disclosure are further described in detail with reference to the accompanying drawings. It should be noted here that the description of these embodiments is intended to facilitate understanding of the present disclosure, but does not constitute a limitation to the present disclosure. Further, the technical features involved in the various embodiments of the present disclosure described below may be combined with each other as long as they do not conflict with each other.

Figure 1:
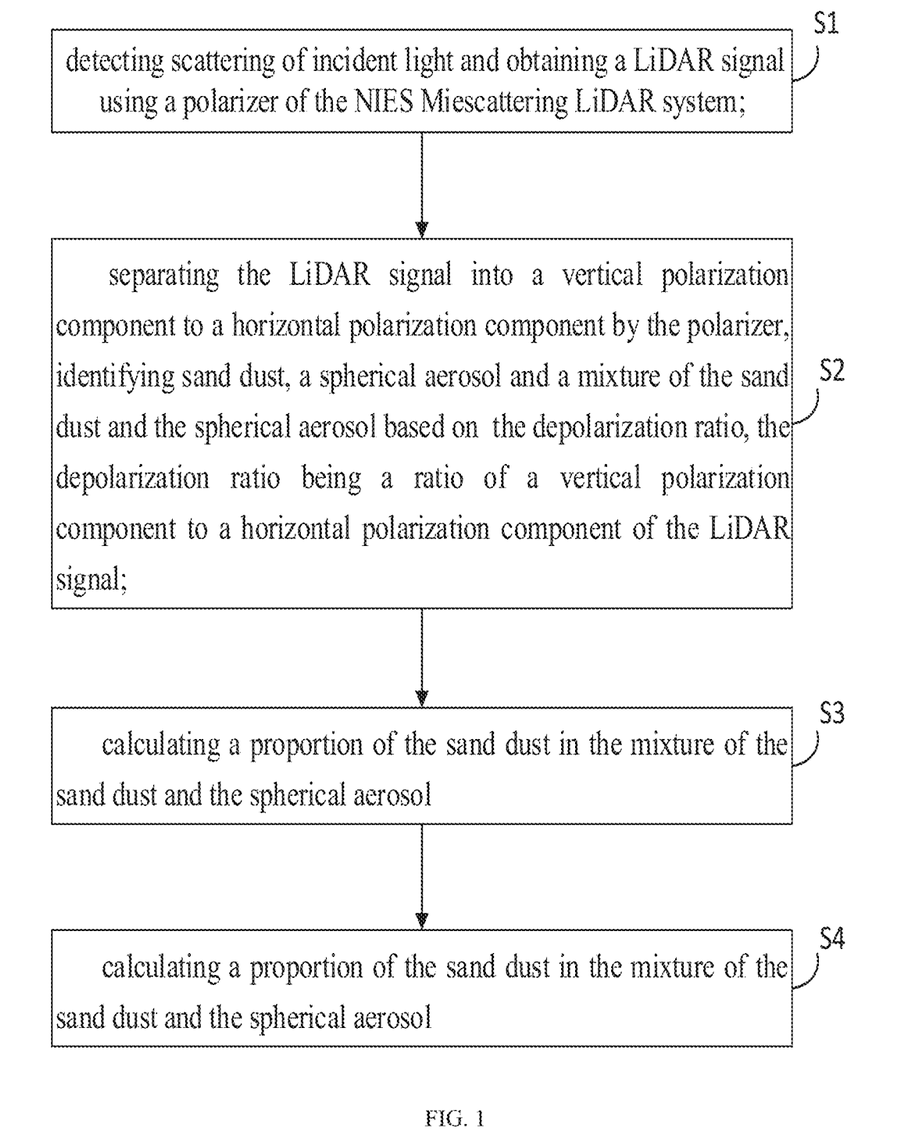
FIG. 1 is a flowchart of a method for inverting aerosol components using a LiDAR ratio and a depolarization ratio by a NIES Miescattering LiDAR system according to the present disclosure.
Figure 2:
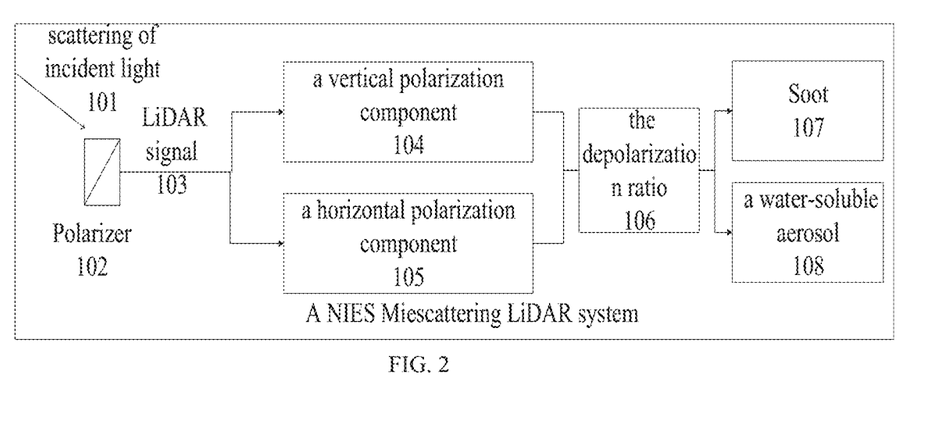
FIG. 2 is system block diagram of a method for inverting aerosol components using a LiDAR ratio and a depolarization ratio by a NIES Miescattering LiDAR system according to the present disclosure.
Figure 3:
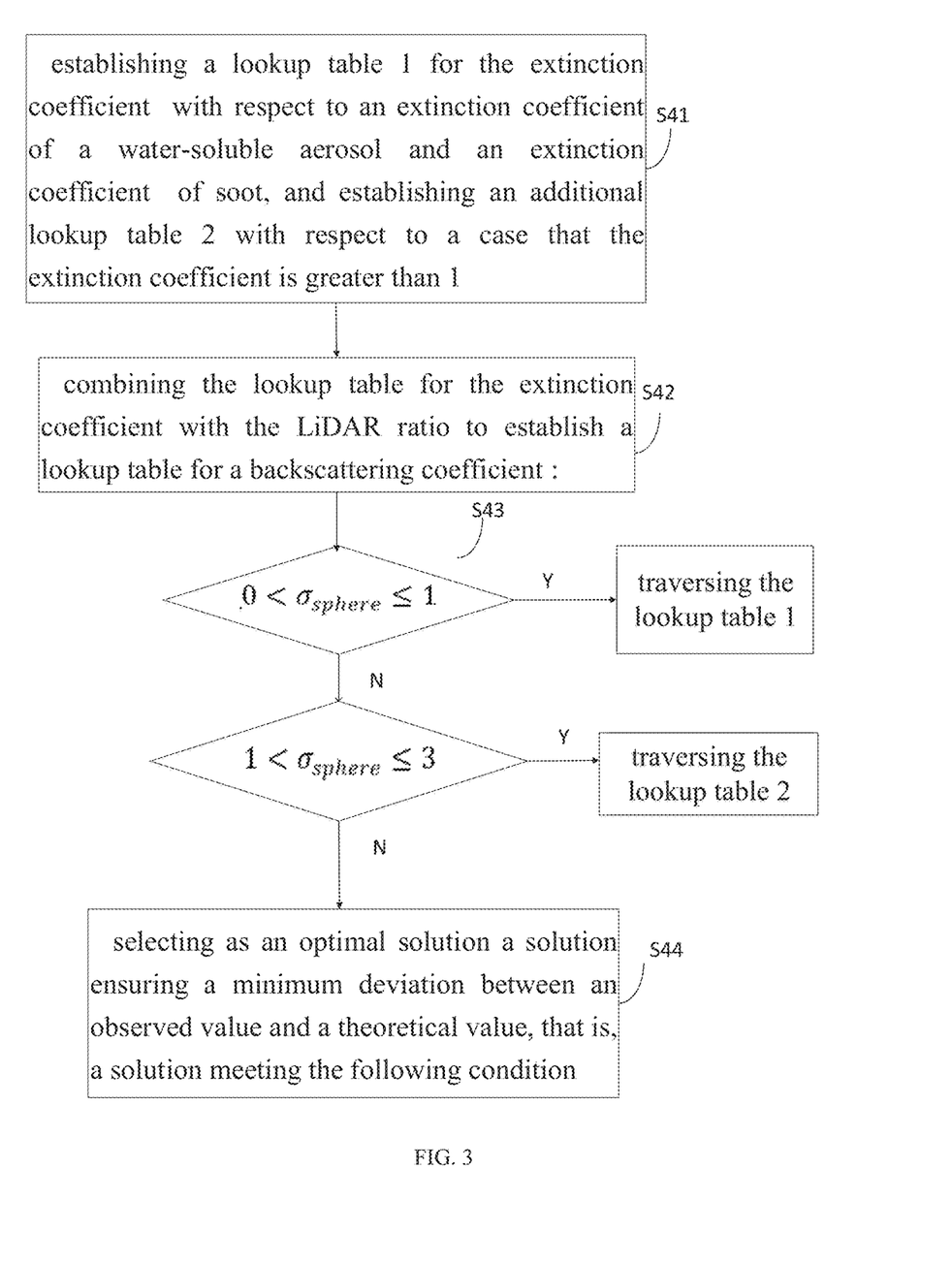
FIG. 3 is a flowchart of a method for identifying soot and a water-soluble aerosol in the spherical aerosol based on a LiDAR ratio.

As shown in FIG. 1 FIG. 2 and FIG. 3, a method for inverting aerosol components using a LiDAR ratio and a depolarization ratio is provided, including steps of: S1. detecting scattering of incident light 101 and obtaining a LiDAR signal 103 using a polarizer 102 of the NIES Miescattering LiDAR system; S2. separating the LiDAR signal 103 into a vertical polarization component 104 to a horizontal polarization component 105 by the polarizer 102, identifying sand dust, a spherical aerosol and a mixture of the sand dust and the spherical aerosol based on the depolarization ratio 106, the depolarization ratio 106 being a ratio of a vertical polarization component 104 to a horizontal polarization component 105 of the LiDAR signal 103; and S3. calculating a proportion of the sand dust in the mixture of the sand dust and the spherical aerosol; and S4. identifying Soot 107 and a water-soluble aerosol 108 in the spherical aerosol based on a LiDAR ratio.

Further, step S3 includes: S41. establishing a lookup table 1 for the extinction coefficient σ with respect to an extinction coefficient $\sigma_{ws}$ of a water-soluble aerosol 108 and an extinction coefficient $\sigma_{st}$ of Soot 107, and establishing an additional lookup table 2 with respect to a case that the extinction coefficient is greater than 1;

S42. combining the lookup table for the extinction coefficient with the LiDAR ratio to establish a lookup table for a backscattering coefficient β:

$$\beta = \frac{\sigma_{ws}}{S_1} + \frac{\sigma_{st}}{S_2}$$

S43. if $0<\sigma_{sphere}\leq1$, traversing the lookup table 1, or if $1<\sigma_{sphere}\leq3$, traversing the lookup table 2, wherein $\sigma_{sphere}$ is an extinction coefficient for the spherical aerosol, $\sigma_{sphere}$ is the backscattering coefficient; and retrieving an array of extinction coefficients from the lookup table whose errors relative to observed values meet a standard:

$$\left|\frac{\sigma_{sphere} - \sigma}{\sigma_{sphere}}\right| < 0.01$$

$$\left|\frac{\beta_{sphere} - \beta}{\beta_{sphere}}\right| < 0.01$$

and S45. if the lookup table does not match the observed values, selecting as an optimal solution a solution ensuring a minimum deviation between an observed value and a theoretical value, that is, a solution meeting the following condition:

$$\min\left(\sqrt{\left|\frac{\sigma_{sphere} - \sigma}{\sigma_{sphere}}\right|^2 + \left|\frac{\beta_{sphere} - \beta}{\beta_{sphere}}\right|^2}\right).$$

In a Fernald inversion method, Miescattering caused by the aerosol and Rayleigh scattering caused by an atmospheric molecule are measured separately (Fernald, 1984), and therefore, a LiDAR equation may be expressed as:

$$P(z)=CP_0 z^{-2}[\beta_1(z)+\beta_2(z)]\exp[-2\int_0^z \sigma_1(z)dz]\exp[-2\int_0^z \sigma_2(z)dz] \quad (8)$$

where C represents a radar correction constant; $P_0$ represents radar transmission power; and β represents the backscattering coefficient, u represents an extinction coefficient, and subscripts of 1 and 2 represent the aerosol particle and the atmospheric molecule respectively.

To solve the equation, a relationship between the extinction coefficient and the backscattering coefficient needs to be assumed, that is, S=σ/β. In this case, the equation (8) can be solved:

$$\beta_1 = -\beta_2 + \frac{X(z)\exp\left[-2(S_1-S_2)\int_{z_c}^z \beta_2(z)dz\right]}{\frac{X(z_c)}{\beta_1(z_c)+\beta_2(z_c)} - 2S_1\int_{z_c}^z P(z)z^2\exp\left[-2(S_1-S_2)\int_{z_c}^z \beta_2(z')dz'\right]dz} \quad (9)$$

where $X(z)=P(z)z^2$; and $\beta_1(z_c)$ and $\beta_2(z_c)$ are boundary values at a far end $z_c$ separately. Herein, $$S_2 = \frac{8\pi}{3}$$

is a fixed value for the atmospheric molecule. In addition, $\beta_2$ is known for an atmospheric model and meteorological observation. Herein, it is assumed that the LiDAR ratio $S_1$ of the aerosol is an empirical value of 50 sr. When optical data of the aerosol provided by AERONET is accurate, the selected LiDAR ratio of the aerosol can also be adjusted based on a calculation result. Therefore, the extinction coefficient of the aerosol is calculated using the equation $\sigma_1=50\beta_1$.

The aerosol depolarization ratio (ADR) is different from the signal depolarization ratio (SDR), and the SDR also covers Rayleigh scattering of the atmospheric molecule. The ADR other than the SDR is required for an aerosol attribute characterized by LiDAR data at a low concentration. The aerosol depolarization ratio can be derived from the signal depolarization ratio and the backscattering coefficient, it is assumed that $$R = \frac{\beta_1+\beta_2}{\beta_2},$$

and therefore, $$\delta = \frac{(1+\delta_m)\delta_v R - (1+\delta_v)\delta_m}{(1+\delta_m)R - (1+\delta_v)}$$

Substituting R into the foregoing equation gives:

$$\delta = \frac{(1+\delta_m)\delta_v R - (1+\delta_v)\delta_m}{(1+\delta_m)R - (1+\delta_v)} \quad (10)$$

where $\delta_v$ represents the signal depolarization ratio; δ represents the aerosol depolarization ratio; and $\delta_m$ represents the molecular depolarization ratio. Herein, 0.0044 is used for calculation. Herein, $\beta_1$ is obtained in the foregoing Fernald inversion method; and $\beta_2$ of the atmospheric molecule can be calculated based on meteorological observation data. It should be noted that the ADR is vulnerable to noise in case of a small backscattering coefficient of the aerosol.

In the step of separating the sand dust from the spherical aerosol, it is considered that the sand dust is mixed with an external part of the spherical aerosol, and aerosol depolarization ratios are $\delta_1$ and $\delta_2$ separately. Herein, the depolarization ratio the depolarization ratios of the two components are defined as $S_i = P_{i\perp}/P_{i\parallel}$, where $P_{i\perp}$ and $P_{i\parallel}$ are vertical and horizontal polarization components of an aerosol backscattered signal respectively. If it is defined that $\delta_i' = P_{i\perp}/(P_{i\perp}+P_{i\parallel})$, $\delta_i' = \delta_i/(\delta_i+1)$. It should be noted that these parameters are all functions of height. If it is assumed that x represents an optical proportion of the sand dust in an aerosol mixture, a polarization component of the backscattered signal can be expressed as:

$$P_\perp = [x\delta_1' + (1-x)\delta_2']P \quad (11)$$

$$P_\parallel = [x(1-\delta_1') + (1-x)(1-\delta_2')]P \quad (12)$$

where $P = P_\perp + P_\parallel$, and therefore, the aerosol depolarization ratio s can be expressed as:

$$\delta = \frac{P_\perp}{P_\parallel} = \frac{x\delta_1' + (1-x)\delta_2'}{x(1-\delta_1') + (1-x)(1-\delta_2')} \quad (13)$$

and therefore, the optical proportion of the sand dust x can be calculated using an equation:

$$x = \frac{(\delta - \delta_2)(1+\delta_1)}{(1+\delta)(\delta_1 - \delta_2)} \quad (14)$$

It should be noted that $\delta$ represents the aerosol depolarization ratio calculated in the equation (10). As shown in Table 1, the depolarization ratio 106 $\delta_1$ of the sand dust and the depolarization ratio 106 $\delta_2$ of the spherical aerosol are 0.31 and 0.05 separately. The extinction coefficient $\sigma_{ds}$ of the sand dust can be expressed as $x\sigma$, and the extinction coefficient $\sigma_{sphere}$ of the spherical aerosol is expressed as $(1-x)\sigma$, where $\sigma$ is the extinction coefficient of the aerosol calculated in the foregoing Fernald method.

Because the water-soluble aerosol $S_1$ (47 sr) and the Soot 107 $S_2$ have significantly different LiDAR ratios (85 sr) as calculated in the Miescattering theory, that is, the two components have significantly different ratios of extinction coefficients to backscattering coefficients, which can be used for distinguishing between the two components. Specific operations are as follows:

(1) Establish a lookup table 1 for the extinction coefficient $\sigma$ with respect to an extinction coefficient $\sigma_{ws}$ of the water-soluble aerosol and an extinction coefficient $\sigma_{st}$ of the Soot 107. The extinction coefficient ranges from 0 km$^{-1}$ to 1 km$^{-1}$, and an interval step of the extinction coefficient of the component is 0.001 km$^{-1}$. In addition, in consideration of an actual situation, the extinction coefficient does not strictly ranges from 0 km$^{-1}$ to 1 km$^{-1}$ under a pollution condition. Therefore, it is necessary to establish an additional lookup table 2 in a case that the extinction coefficient is greater than 1, an upper limit of the extinction coefficient is 3 km$^{-1}$ (selected based on AERONET data), and the interval step is 0.005 km$^{-1}$.

(2) Combine the lookup table for the extinction coefficient with the LiDAR ratio to establish a lookup table for a backscattering coefficient $\beta$:

$$\beta = \frac{\sigma_{ws}}{S_1} + \frac{\sigma_{st}}{S_2} \quad (15)$$

(3) Based on the extinction coefficient $\sigma_{sphere}$ and the backscattering coefficient $\beta_{sphere}$ of the spherical aerosol calculated in the step of separating the sand dust from the spherical aerosol, and if $0 < \sigma_{sphere} \leq 1$, traverse the lookup table 1; or if $1 < \sigma_{sphere} \leq 3$, traverse the lookup table 2, to retrieve an array of extinction coefficients from the lookup table whose errors relative to observed values meet a standard.

$$\left|\frac{\sigma_{sphere} - \sigma}{\sigma_{sphere}}\right| < 0.01 \quad (16)$$

$$\left|\frac{\beta_{sphere} - \beta}{\beta_{sphere}}\right| < 0.01 \quad (17)$$

(4) If the lookup table does not match the observed values, select as an optimal solution a solution ensuring a minimum deviation between an observed value and a theoretical value, that is, a solution meeting the following condition:

$$\min\left(\sqrt{\left|\frac{\sigma_{sphere} - \sigma}{\sigma_{sphere}}\right|^2 + \left|\frac{\beta_{sphere} - \beta}{\beta_{sphere}}\right|^2}\right) \quad (18)$$

Figure 4:
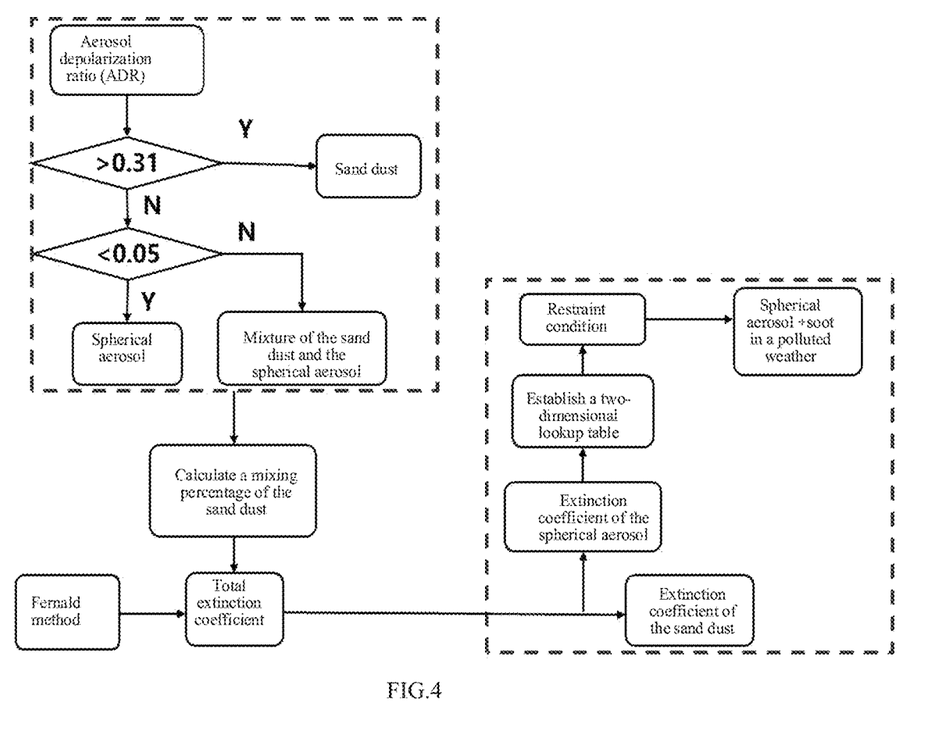
FIG. 4 is a flowchart of a method for inverting aerosol components using a LiDAR ratio and a depolarization ratio according to the present disclosure.
Figure 5:
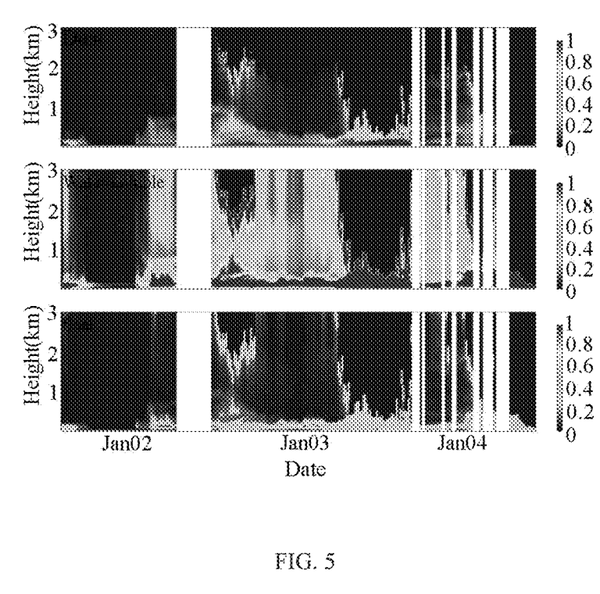
FIG. 5 is a diagram of testing a heavily polluted weather in a method for inverting aerosol components using a LiDAR ratio and a depolarization ratio according to the present disclosure.
Figure 6:
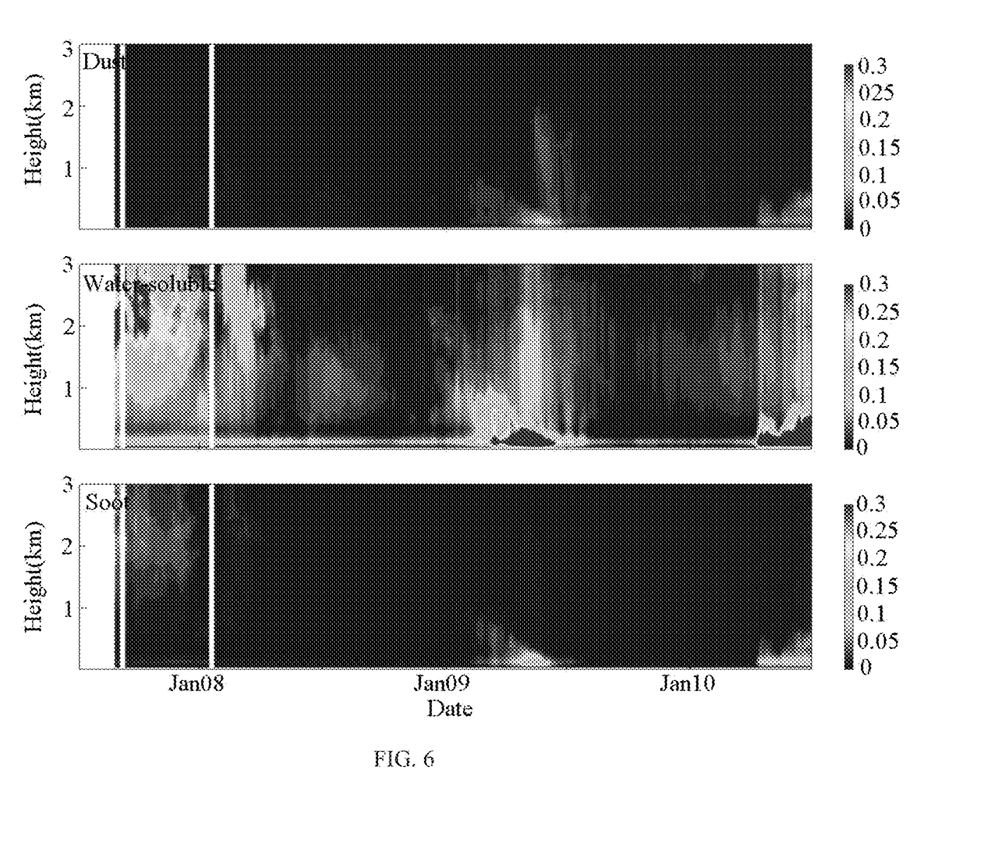
FIG. 6 is a diagram of testing a clear weather in a method for inverting aerosol components using a LiDAR ratio and a depolarization ratio according to the present disclosure.

In the present disclosure, the solution may be achieved in a method for inverting aerosol components using a LiDAR ratio and a depolarization ratio with a requirement of only a wavelength with a polarization channel. The method was applied to actually observed data of the LiDAR in 2017, and the data in a heavily polluted weather (FIG. 4) and a clean weather (FIG. 5) was calculated. Inversion results of aerosol components from January 2 to Jan. 4, 2017 are shown in FIG. 2. It can be seen that under the heavily polluted weather, the sand dust is not close to the ground, and the water-soluble aerosol and the Soot 107 are dominant. Inversion results of aerosol components from January 8 to Jan. 10, 2017 are shown in FIG. 5. Under the clean weather, there is almost no sand dust, the Soot 107 does not have a high concentration, and water-soluble aerosols such as sulfate and nitrate are dominant.

The embodiments of the present disclosure are described in detail above with reference to the accompanying drawings, but the present disclosure is not limited to the described embodiments. For a person skilled in the art, changes, modifications, replacements, and variations made to these embodiments without departing from the principle and spirit of the present disclosure shall still fall within the protection scope of the present disclosure.

What is claimed is:

1. A method for inverting aerosol components using a LiDAR ratio and a depolarization ratio by a NIES Miescattering LiDAR system, comprising the steps of:
   S1) detecting scattering of incident light and obtaining a LiDAR signal using a polarizer of the NIES Miescattering LiDAR system;
   S2) separating the LiDAR signal into a vertical polarization component to a horizontal polarization component by the polarizer, identifying sand dust, a spherical aerosol and a mixture of the sand dust and the spherical aerosol based on the depolarization ratio, the depolarization ratio being a ratio of a vertical polarization component to a horizontal polarization component of the LiDAR signal;

S3) calculating a proportion of the sand dust in the mixture of the sand dust and the spherical aerosol; and S4) identifying soot and a water-soluble aerosol in the spherical aerosol based on a LiDAR ratio, wherein step S4 comprises:

S41) establishing a lookup table 1 for the extinction coefficient σ with respect to an extinction coefficient $\sigma_{ws}$ of a water-soluble aerosol and an extinction coefficient $\sigma_{st}$ of soot, and establishing an additional lookup table 2 with respect to a case that the extinction coefficient is greater than 1;

S42) combining the lookup table for the extinction coefficient with the LiDAR ratio to establish a lookup table for a backscattering coefficient β:

$$\beta = \frac{\sigma_{ws}}{S_1} + \frac{\sigma_{st}}{S_2}$$

S43) if $0<\sigma_{sphere}\leq 1$, traversing the lookup table 1, or if $1<\sigma_{sphere}\leq 3$, traversing the lookup table 2, wherein $\sigma_{sphere}$ is an extinction coefficient for the spherical aerosol, $\sigma_{sphere}$ is the backscattering coefficient; and retrieving an array of extinction coefficients from the lookup table whose errors relative to observed values meet a standard:

$$\left|\frac{\sigma_{sphere}-\sigma}{\sigma_{sphere}}\right|<0.01$$

$$\left|\frac{\beta_{sphere}-\beta}{\beta_{sphere}}\right|<0.01$$

and

S45) if the lookup table does not match the observed values, selecting as an optimal solution a solution ensuring a minimum deviation between an observed value and a theoretical value, that is, a solution meeting the following condition:

$$\min\left(\sqrt{\left|\frac{\sigma_{sphere}-\sigma}{\sigma_{sphere}}\right|^2 + \left|\frac{\beta_{sphere}-\beta}{\beta_{sphere}}\right|^2}\right).$$

2. The method for inverting aerosol components using a LiDAR ratio and a depolarization ratio according to claim 1, wherein step S2 comprises: calculating an aerosol depolarization ratio (ADR), wherein when the ADR is greater than 0.31, the aerosol components are considered to be the sand dust; when 0.05≤ADR≤0.31, the aerosol components are considered to be the mixture of the sand dust and the spherical aerosol; or when the ADR is less than 0.05, the aerosol components are considered to be the spherical aerosol.

3. The method for inverting aerosol components using a LiDAR ratio and a depolarization ratio according to claim 2, wherein the calculating the ADR comprises: directing the LiDAR signal through the polarizer with a 45° polarization direction at a 532 nm signal using the NIES Miescattering LiDAR system, to separate a horizontal signal from a vertical signal.

4. The method for inverting aerosol components using a LiDAR ratio and a depolarization ratio according to claim 1, wherein step S3 comprises the steps of:

S31) setting depolarization ratios of the sand dust and the spherical aerosol as $\delta_1$ and $\delta_2$ respectively, and defining the depolarization ratios of the sand dust and the spherical aerosol as $\delta_i = P_{i\perp}/P_{i\parallel}$, wherein $P_{i\perp}$ and $P_{i\parallel}$ are vertical and horizontal polarization components of an aerosol backscattered signal respectively;

S32) defining $\delta_i' = P_{i\perp}/(P_{i\perp}+P_{i\parallel})$, then $\delta_i' = \delta_i/(\delta_i+1)$; and S33) assuming that x represents an optical proportion of the sand dust in an aerosol mixture, wherein a polarization component of the backscattered signal is expressed as:

$$P_\perp = [x\delta_1' + (1-x)\delta_2']P$$

$$P_\parallel = [x(1-\delta_1') + (1-x)(1-\delta_2')]P$$

wherein $P = P_\perp + P_\parallel$, and therefore, the aerosol depolarization ratio δ is expressed as:

$$\delta = \frac{P_\perp}{P_\parallel} = \frac{x\delta_1' + (1-x)\delta_2'}{x(1-\delta_1') + (1-x)(1-\delta_2')}$$

and therefore, the optical proportion of the sand dust x can be calculated using an equation:

$$x = \frac{(\delta-\delta_2)(1+\delta_1)}{(1+\delta)(\delta_1-\delta_2)}.$$

5. The method for inverting aerosol components using a LiDAR ratio and a depolarization ratio according to claim 4, wherein the aerosol depolarization ratio δ is obtained through the following steps:
assuming $$R = \frac{\beta_1+\beta_2}{\beta_2},$$

wherein $\beta_1$ represents a backscattering coefficient of an aerosol particle, and $\beta_2$ represents a backscattering coefficient of an atmospheric molecule; and $$\delta = \frac{(1+\delta_m)\delta_v R - (1+\delta_v)\delta_m}{(1+\delta_m)R - (1+\delta_v)}$$

substituting R into the equation:

$$\delta = \frac{(1+\delta_m)\delta_v R - (1+\delta_v)\delta_m}{(1+\delta_m)R - (1+\delta_v)}$$

wherein $\delta_v$ represents a signal depolarization ratio, and $\delta_m$ represents a molecule depolarization ratio.

6. The method for inverting aerosol components using a LiDAR ratio and a depolarization ratio according to claim 5, wherein $\beta_1$ is obtained through the following steps:
measuring the Miescattering caused by the aerosol and the Rayleigh scattering caused by the atmospheric molecule separately, wherein a LiDAR equation is expressed as $$P(z)=CP_0z^{-2}[\beta_1(z)+\beta_2(z)]\exp[-2\int_0^z\sigma_1(z)dz]\exp[-2\int_0^z\sigma_2(z)dz]$$

wherein C represents a radar correction constant; $P_0$ represents radar transmission power; and $\beta$ represents the backscattering coefficient, $\sigma$ represents an extinction coefficient, and subscripts of 1 and 2 represent the aerosol particle and the atmospheric molecule respectively;

assuming that a relationship between the extinction coefficient $\sigma$ and the backscattering coefficient $\beta$ is as follows:

$$S=\sigma/\beta$$

and solving the foregoing LiDAR equation gives:

$$\beta_1 = -\beta_2 + \frac{X(z)\exp\left[-2(S_1-S_2)\int_{z_c}^z \beta_2(z)dz\right]}{\frac{X(z_c)}{\beta_1(z_c)+\beta_2(z_c)} - 2S_1\int_{z_c}^z P(z)z^2\exp\left[-2(S_1-S_2)\int_{z_c}^z \beta_2(z')dz'\right]dz}$$

wherein $X(z)=P(z)z^2$; and $\beta_1(z_c)$ and $\beta_2(z_c)$ are boundary values at a far end $z_c$.

7. The method for inverting aerosol components using a LiDAR ratio and a depolarization ratio according to claim 1, wherein in step S43, the extinction coefficient $\sigma_{sphere}$ of the spherical aerosol is equal to $(1-x)\sigma$.

\* \* \* \* \*